US010967120B2

(12) United States Patent
Lorenz (10) Patent No.: US 10,967,120 B2
(45) Date of Patent: Apr. 6, 2021

(54) PORTABLE LIQUID DRUG DELIVERY DEVICE

(71) Applicant: Roche Diabetes Care, Inc., Indianapolis, IN (US)

(72) Inventor: Markus Lorenz, Karlsruhe (DE)

(73) Assignee: Roche Diabetes Care, Inc., Indianapolis, IN (US)

( * ) Notice: Subject to any disclaimer, the term of this patent is extended or adjusted under 35 U.S.C. 154(b) by 79 days.

(21) Appl. No.: 16/255,156

(22) Filed: Jan. 23, 2019

(65) Prior Publication Data
US 2019/0175824 A1     Jun. 13, 2019

Related U.S. Application Data

(63) Continuation of application No. PCT/EP2017/069481, filed on Aug. 1, 2017.

(30) Foreign Application Priority Data

Aug. 25, 2016    (EP) ..................................... 16185739

(51) Int. Cl.
*A61M 5/142* (2006.01)
*A61M 5/145* (2006.01)
*A61M 5/172* (2006.01)

(52) U.S. Cl.
CPC ...... *A61M 5/14248* (2013.01); *A61M 5/1456* (2013.01); *A61M 5/172* (2013.01);
(Continued)

(58) Field of Classification Search
CPC ............ A61M 5/14248; A61M 5/1456; A61M 2005/14268; A61M 5/14573
See application file for complete search history.

(56) References Cited

U.S. PATENT DOCUMENTS 6,423,035 B1 *  7/2002  Das ..................... A61M 5/1456
                                                    128/DIG. 1
2008/0051711 A1  2/2008  Mounce et al.
(Continued)

FOREIGN PATENT DOCUMENTS

WO    WO 2009/125398 A2    10/2009

OTHER PUBLICATIONS

International Preliminary Report on Patentability, PCT/EP2017/069481, dated Feb. 26, 2019, 9 pages.
(Continued)

*Primary Examiner* — Nathan R Price
*Assistant Examiner* — Dung T Ulsh
(74) *Attorney, Agent, or Firm* — Bose McKinney & Evans LLP (57) ABSTRACT

A portable liquid drug delivery device has a reservoir part and a driving part, and the driving part has a drive that produces a torque. The reservoir part has a reservoir that retains liquid drug and an outlet port is in fluid communication with the reservoir. An engagement member has an inner thread that engages the thread of a piston rod in an engaged position and is disengaged from the thread of the piston rod in a disengaged position. The engagement member is prestressed in the disengaged position to thereby bias the engagement member toward the engaged position. The engagement member only converts the torque of the drive into a linear movement of the piston rod when the engagement member is in the engaged position. The piston is configured, upon the linear movement of the piston rod, to deliver the liquid drug to the outlet port.

15 Claims, 3 Drawing Sheets

(52) U.S. Cl.
CPC ............. *A61M 2005/14268* (2013.01); *A61M 2005/14573* (2013.01)

(56) References Cited

U.S. PATENT DOCUMENTS

| | | | | |
|---|---|---|---|---|
| 2009/0143735 A1* | 6/2009 | De Polo | ............... | A61M 5/1456 604/155 |
| 2011/0213329 A1* | 9/2011 | Yodfat | ............... | A61M 5/14248 604/500 |
| 2012/0022453 A1* | 1/2012 | Yodfat | ............... | A61M 5/31515 604/155 |
| 2016/0067403 A1 | 3/2016 | Moberg et al. | | |
| 2018/0038361 A1* | 2/2018 | Werner | ................ | F04B 39/121 |

OTHER PUBLICATIONS

International Seach Report and Written Opinion of the International Searching Authority, PCT/EP2017/069481, dated Nov. 7, 2017, 10 pages.

\* cited by examiner

PORTABLE LIQUID DRUG DELIVERY DEVICE

RELATED APPLICATIONS

This application is a continuation of PCT/EP2017/069481, filed on Aug. 1, 2017, which claims priority to EP 16 185 739.6, filed on Aug. 25, 2016, the entire disclosures of both of which are hereby incorporated herein by reference.

BACKGROUND

This disclosure relates to a portable liquid drug delivery device, as well as a reservoir part for a portable liquid drug delivery device.

Drug delivery devices are medical devices that provide prescribed fluids to patients. For example, medication such as antibiotics, chemotherapy drugs and insulin are commonly delivered to patients via a drug delivery device. For example, WO 2009/125398 A2 discloses a portable therapeutic fluid dispensing device which includes a reusable part comprising a reusable part housing including at least a controller in the first portion of a driving mechanism, and a disposable part comprising a disposable part housing including at least a reservoir to retain the therapeutic fluid, an outlet port to which the therapeutic fluid is dispensed, a fluid conduit providing fluid communication between the reservoir and the outlet port, and the second portion of the driving mechanism.

This disclosure teaches an improved portable liquid drug delivery device and an improved reservoir part for such a portable liquid drug delivery device.

Embodiments relate to a portable liquid drug delivery device comprising a driving part comprising a driving mechanism and a reservoir part comprising:
  a reservoir adapted to retain a liquid drug,
  an outlet port in fluid communication with the reservoir,
  a threaded piston rod with a piston,
  an engagement member having an inner thread configured to engage with the thread of the piston rod in an engagement position and to disengage from the thread of the piston rod in a disengagement position, the engagement member being prestressed in the disengagement position, the prestress being adapted to force the engagement member to move from the disengagement position to the engagement position, the engagement member being adapted for only converting in the engagement position torque of the driving mechanism into a linear movement of the piston rod, the piston rod being adapted upon the linear movement of the piston rod to deliver the liquid drug to the outlet port.

Embodiments may thus provide for a portable liquid drug delivery device in which by linear movement of the threaded piston rod the liquid drug is pressed by the piston towards the outlet port. Since the engagement member is configured to have two positions that include an engagement position and a disengagement position, it may be possible to enable pushing or pulling of the piston rod during priming or reservoir filling in the disengagement position and to restrict the displacement of the piston rod during operation of the portable liquid drug delivery device in the engagement position.

Since the engagement member is prestressed in the disengagement position with the prestress being adapted to force the engagement member to move from the disengagement position to the engagement position, the operational force that has to be brought up by a user of the portable liquid drug delivery device in order to bring the device to an operational mode, i.e., a mode in which the engagement member is in the engagement position, may be minimized. The prestress may support the user to move the engagement member from the disengagement position to the engagement position, which may be of significant benefit especially for elderly people who typically do not any longer have the power to mechanically manipulate the engagement member. Thus, the operational force may be minimized while still maintaining the possibility to distinguish between the engagement and the disengagement position, allowing for both an operational use of the reservoir part with the portable liquid drug delivery device as well during priming or reservoir filling.

In accordance with an embodiment of this disclosure, the engagement member is adapted to automatically move from the disengagement position to the engagement position upon a mechanical coupling of the reservoir part with the driving part. Thus, upon the mechanical coupling of the reservoir part with the driving part, the piston rod is automatically coupled with the driving mechanism in such a manner, that a rotational movement of the driving mechanism is transformed into the linear movement of the piston rod in order to deliver the liquid drug to the outlet port.

The automatic movement of the engagement member from the disengagement position to the engagement position has the advantage that the operational readiness of the drug delivery device is automatically guaranteed. Thus, the situation is avoided that a user of the drug delivery device may forget to move the engagement member from the disengagement position to the engagement position and thus lacks the provision of the liquid drug even though the driving mechanism is operating, i.e., performing a rotational movement.

In accordance with an embodiment of this disclosure, the piston rod is:
  rotatable with respect to the reservoir part and adapted for being directed or rotatory coupled to the driving mechanism upon the mechanical coupling of the reservoir part with the driving part, the engagement member being fixed with respect to the reservoir part or
  non-rotatable with respect to the reservoir part and adapted for being indirectly mechanically coupled to the driving mechanism via the engagement member, the engagement member being adapted for being directly rotatory coupled to the driving mechanism upon the mechanical coupling of the reservoir with the driving part.

Thus, in the first alternative the driving mechanism may directly rotate the piston rod, which in the engagement position of the engagement member is winding itself up within the, e.g., nut-shaped engagement member.

In the second alternative, the, e.g., nut-shaped engagement member is rotated by the driving mechanism while the piston rod itself is non-rotatable with respect to the reservoir part. Since nevertheless the piston rod and the engagement member are engaged with respect to each other in the engagement position, the rotation of the engagement member leads to a linear movement of the piston rod and thus the piston inside the reservoir.

In accordance with an embodiment of this disclosure, in the engagement position on the circumference of the piston rod the threads of the piston rod fully engage with the threads of the engagement member. This may have the advantage that the mechanical stability that may be described for example by the stiffness of the interface between the piston rod and the engagement member may be significantly enhanced compared to a scenario in which the piston rod is only partially guided by the engagement member. This may increase the probability that even in case of a mechanical force acting onto the portable drug delivery device from outside the operation of the drug delivery device is not negatively influenced in such a manner that for example the threads of the piston rod and the threads of the driving mechanism are not fully meshing with each other anymore.

In accordance with an embodiment of this disclosure, the prestress is the result of anyone of the following: an inner prestress of the engagement member, an elastic element inducing the prestress onto the engagement member. Having an inner prestress of the engagement member may have the advantage of a simple mechanical setup for which the space occupied by the engagement member is minimized. Using an elastic element like for example a rubber band or a spring may have the advantage that the durability of the engagement member is enhanced.

In accordance with an embodiment of this disclosure, the engagement member comprises a nut, the nut comprising two parts with threads, the two parts:
  clutching the piston rod in the engagement position such that the threads of the two parts are engaging with the threads of the piston rod,
  release the piston rod in the disengagement position such that the threads of the two parts are disengaged from the threads of the piston rod.

Again, as mentioned above, in the engagement position the threads of the two parts are for example completely engage with the threads of the piston rod.

In accordance with an embodiment of this disclosure, the two parts are joined with each other by a hinge, wherein the engagement member is adapted such that the movement of the engagement member from the disengagement position to the engagement position comprises a swiveling of the two parts towards each other around the hinge. This may have the advantage, that again the mechanical setup of the drug delivery device can be simplified. In accordance with an embodiment, the two parts and the hinge are connected with each other by a substance-to-substance bond. For example, the engagement member may be manufactured together using a single injection molding process and one common mold.

In accordance with an embodiment of this disclosure, the portable drug delivery device further comprises a handle, the handle being adapted in the disengagement position for blocking the movement of the two parts from the disengagement position to the engagement position. Usage of a handle may have the advantage that the movement of the two parts from the disengagement position to the engagement position can be easily initiated by suspending the blocking of the two parts such that thereupon the two parts are automatically moving themselves towards the engagement position due to the prestress available with the two parts. Again, the operational force to suspend the blocking by the handle can therefore be rather low.

In accordance with an embodiment of this disclosure, each part comprises an arm, wherein:
  in the disengagement position the handle is located in between the arms and adapted for blocking the movement of the two parts from the disengagement position to the engagement position,
  in the engagement position the handle is retracted from the arms to the extent that the two parts can take the engagement position.

In accordance with a further embodiment of this disclosure, the handle is further adapted to automatically move the two parts apart from each other from the engagement position towards the disengagement position upon a mechanical decoupling of the reservoir part from the driving part. Alternatively, it is possible that by a direct user operation of the handle, the two parts are moved apart from each other from the engagement to the disengagement position for example in case the reservoir part is detached from the driving part. Thus, in general due to a mechanical force acting upon the handle the handle moves the two parts apart from each other, wherein the mechanical force is the result either of a decoupling of the reservoir part from the driving part or a user-initiated mechanical force.

In accordance with an embodiment of this disclosure, the handle comprises a mandrel, the mandrel being adapted for being located in between the two parts for blocking the movement of the two parts from the disengagement position to the engagement position, the mandrel and the two parts being shaped such that the mandrel forces the movement of the two parts apart from each other from the engagement position towards the disengagement position upon the mechanical force acting upon the handle. Again, the mechanical force acting upon the handle may for example be either the result of the mechanical decoupling of the reservoir part from the driving part or due to a user-initiated force acting upon the handle. The user may push or pull or rotate the handle for this purpose.

This embodiment may have the advantage that in a mechanically easy manner the two parts can be moved from the engagement position to the disengagement position. For example, the two parts may have a common hole that is formed in the engagement position and that is adapted to receive the mandrel. In case the mandrel is conically formed, pressing the mandrel into the hole results in a gradual sliding of the two parts away from each other, the more, the conically-shaped mandrel is moving between the two parts.

An alternative possibility would be that the two arms are V-shaped and that the cylindrical mandrel is laterally moved towards the piston rod in a plane perpendicular to the axis of the piston rod.

In accordance with a further embodiment of this disclosure, the handle is mounted in a pivoted way around an axis on the reservoir part, the handle being adapted for performing a rotation around the axis in between the engagement position and the disengagement position. Alternatively, the handle is mounted on the reservoir part in a laterally movable manner and the lateral movement is a movement in a plane perpendicular to the axis of the piston rod, as discussed above.

In accordance with a further embodiment of this disclosure, the driving part is a reusable part and the reservoir part is a disposable part.

In another aspect, this disclosure relates to a reservoir part for a portable liquid drug delivery device as described above.

It is understood that one or more of the aforementioned disclosed embodiments may be combined as long as the combined embodiments are not mutually exclusive.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
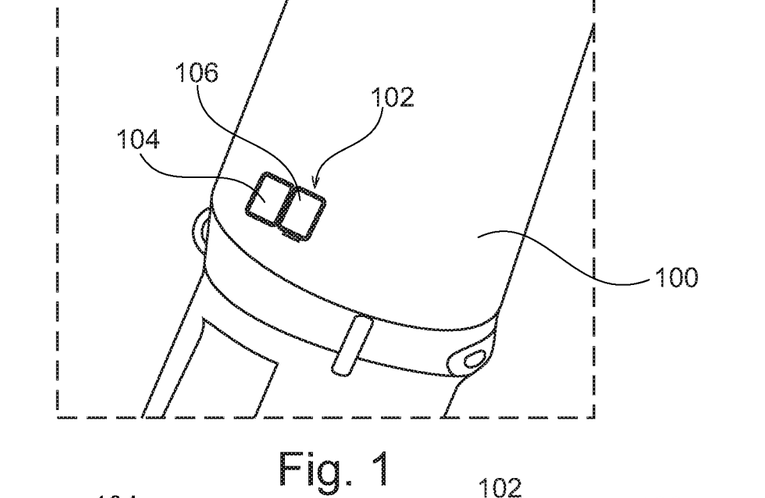
FIG. 1 is a schematic diagram of a portable liquid drug delivery device carried by a user.
Figure 2:
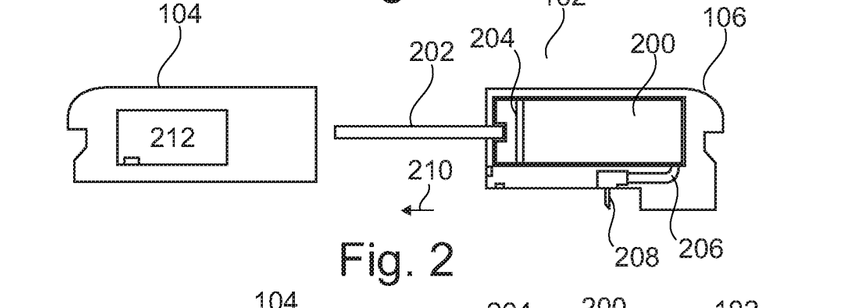
FIG. 2 is a schematic block diagram of a portable liquid drug delivery device in which the driving part is separated from the reservoir part.

FIG. 1 illustrates a schematic diagram of a portable liquid drug delivery device 102 that is currently carried by a user or a patient 100. The portable liquid drug delivery device 102 is adhered to the skin of the patient 100 and comprises two parts, namely a driving part 104 (also referred to as a "drive module") and a reservoir part 106 (also referred to as a "reservoir module"). The driving part 104 is preferably reusable and it can be coupled to a base to mate with the reservoir part 106 which is for example a disposable part, to enable operation of the portable liquid drug delivery device 102. FIG. 2 shows a schematic block diagram of the portable liquid drug delivery device 102 in a state, where the driving part 104 and the reservoir part 106 are still separated from each other. The reservoir part 106 comprises a reservoir 200 from which a fluid contained in the reservoir is delivered to an outlet port 208 via a connecting tube 206. Located within the reservoir 200 is a piston 204 which can be pushed and pulled forth and back via a threaded piston rod 202. The actuation of the piston 204 is performed by a driving mechanism or drive 220 that is in the driving part 104.

The reservoir part 106 and the driving part 104 may be coupled together by moving the reservoir part 106 in direction 210 towards the driving part 104. Then, the driving part 104 and the reservoir part 106 may lock in place. As a result, the threaded piston rod may be coupled to the driving mechanism 212 in such a manner that an operation of the driving mechanism 212 leads to a movement of the piston rod 202 and thus the piston 204 towards direction 310. As a result, a liquid drug contained in the reservoir 200 is pressed through the connecting tube 206 towards the outlet port 208.

Figure 3:
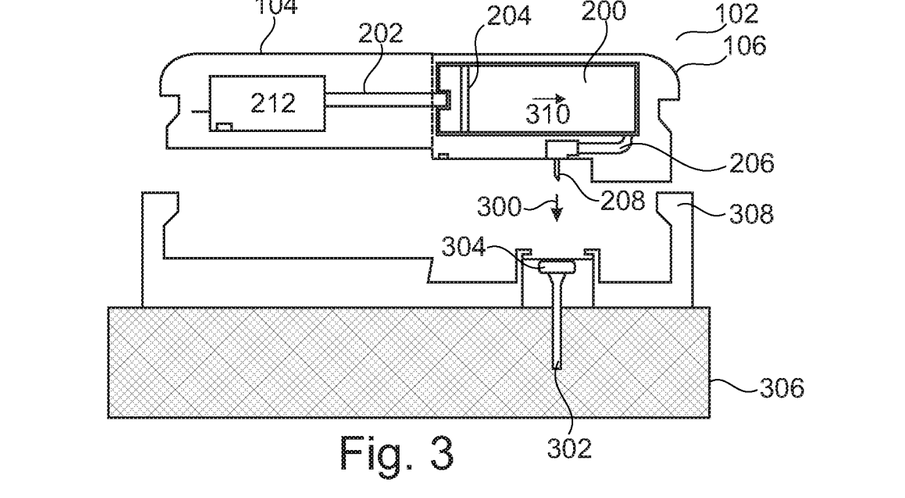
FIG. 3 is a block diagram of the portable liquid drug delivery device of FIG. 2 in a state in which the driving part is connected to the reservoir part.

This is shown in more detail in FIG. 3 which besides the joint driving part and reservoir part additionally shows the base 308 that is attached to a skin 306 of the patient or user 100. The joint driving part and reservoir part can be connected and disconnected from the base at the user's discretion.

The base 308 may comprise for example a cannula cartridge unit which includes a cannula 302 which on top may have a self-sealing septum 304 through which a penetrating member (not shown in FIG. 3) may be inserted. Said penetrating member may include a sharp tip and may be configured to penetrate the skin 306 of the patient to allow insertion and placement of the cannula in the subcutaneous tissue.

The septum 304 is configured to be repeatedly pierced by the outlet port 208. For that purpose, the outlet port 208 may comprise a connecting lumen.

Figure 4:
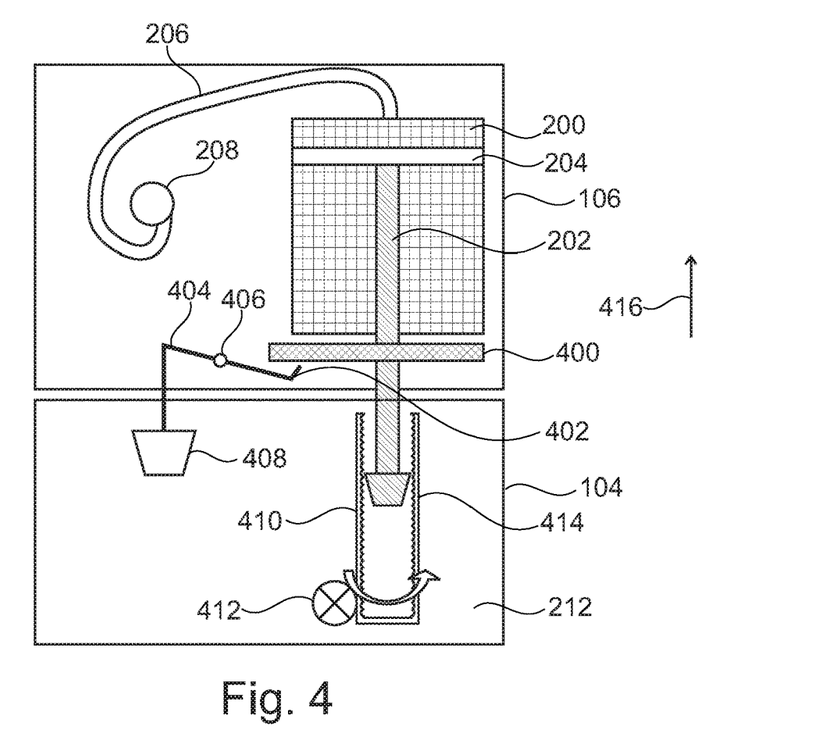
FIG. 4 is a block diagram of a further portable liquid drug delivery device.

FIG. 4 illustrates a block diagram which shows further details of both the driving part 104 and the reservoir part 106. The driving part comprises the driving mechanism 212 which comprises a motor 412 and a sleeve 410 rotationally coupled to the motor 412. The motor 412 is thus adapted to provide a torque force onto a sleeve 410. The sleeve 410 is threaded and is adapted to receive a threaded drive nut 414 that is mechanically fixed to the proximal end of the threaded piston rod 202. As a result, the torque acting onto the drive nut results in a rotation of the piston rod. It has to be noted here that the drive nut can be freely moved along the rotating sleeve 410 while the rotation of the drive nut 414 itself does not automatically lead to a translational linear movement of the drive nut and thus the piston rod 202 in a direction 416 towards the reservoir. The linear movement towards the reservoir and thus in direction 416 is the result of the presence of an engagement member 400 of the reservoir part 106.

In the present example of FIG. 4 the engagement member 400 is fixed with respect to the reservoir part 106 in such a manner that it is itself not able to rotate, for example due to a rotation of the rotating sleeve 410 or the piston rod 202.

It has to be noted here that as an alternative it is possible that the rotating sleeve 410 is not mechanically coupled to the piston rod 202 via the driving nut 414, but that the rotating sleeve 410 is coupled to the engagement member 400 in such a manner that the rotation of the rotating sleeve 410 also results in a direct rotation of the engagement member 400. In this example, the piston rod 202 is not rotatable at all such that the rotation of the engagement member 400 results in a screwing of the piston rod 202 in direction 416. The result is the same as described above, namely, that the liquid drug contained in the reservoir 200 is pressed through the connecting tube 206 to the outlet port 208.

In the example of FIG. 4 the engagement member 400 is adapted for converging in a so called 'engagement position' or 'engaged position' a torque of the driving mechanism 212, i.e., in the present example a rotation of the piston rod 202 into a linear movement of the piston rod in direction 416. For example, the engagement member is nut-shaped with threads that are engaging with respective threads of the threaded piston rod 202. Since the engagement member 400 is fixed as described above, a rotation of the piston rod will therefore lead to a linear movement of the piston rod 202 in direction 416—the piston rod 202 is screwing itself up into direction 416 thus moving the piston 204 up for decreasing the volume available for the liquid drug in the reservoir 200 and therefore pressing the liquid drug through the connecting tube 206 to the outlet port 208.

Since it may be desired that only in the operational state the piston rod can be moved into direction 416 by rotating the piston rod and that for example for refilling the reservoir 200 the piston rod 202 is freely moveable opposed to direction 416 by pulling the piston rod 202, the engagement member 400 can be moved in between the just described engagement position and a disengagement position (or "disengaged position").

In order to move the engagement member from the disengagement position to the engagement position, a handle 404 is provided which is mounted in a pivoted way around an axis 406 on the reservoir part 106. The handle is adapted for performing a rotation around the axis 406. In the engagement position that is illustrated in FIG. 4 due to the locking of the driving part 104 with the reservoir part 106 a counterpart 408 is pressed against the handle 404 in such a manner that a mandrel 402 of the handle 404 is disengaged from the engagement member 400.

Figure 5A:
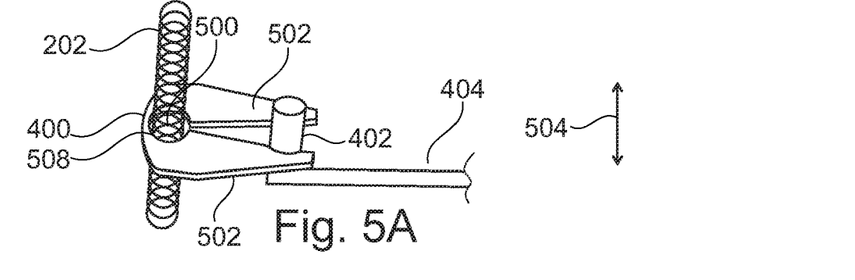
FIGS. 5A and 5B schematically illustrate the engagement member in a disengagement position and an engagement position.
Figure 5B:
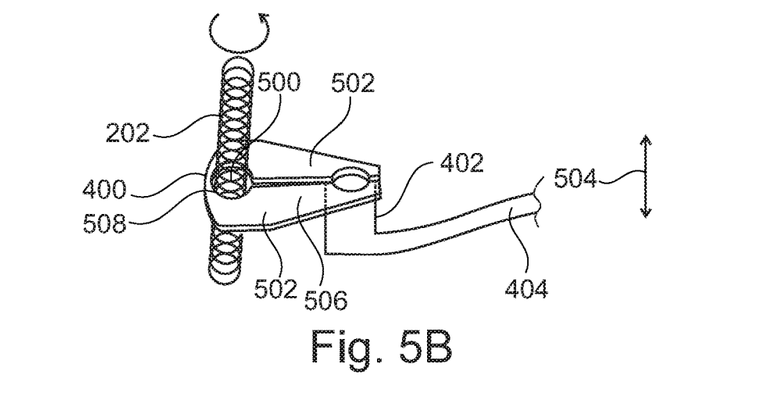

The transition from the engagement of the mandrel 404 with the engagement member 400 to the disengagement of said mandrel 402 is illustrated more specifically in FIGS. 5a and 5b.

FIG. 5a schematically illustrates the threaded piston rod 202 that is received within a threaded counterpart 500 of the engagement member 400. The engagement member 400 comprises two arms 502 which are separated from each other by the mandrel 402 of the handle 404. In other words, the mandrel 402 is located in between the two arms 502 thus blocking a further movement of the two arms 502 towards each other. In this state, the piston rod is released such that the threads of the two parts 502 are disengaged from the threads of the piston rod 202.

In the disengagement position as just discussed with respect to FIG. 5a, the piston rod 202 is freely moveable in direction 504 without any need of rotating the piston rod 202 for that purpose.

In contrast thereto, in FIG. 5b the handle 404 has been moved in direction 504 such that the mandrel 402 is now retracted from the two arms 502. Due to a prestress that may for example be due to an inner prestress of the engagement member, the two arms 502 have moved towards each other. As a result, the engagement member has moved from the disengagement position discussed with reference to FIG. 5a to an engagement position as shown in FIG. 5b. In this engagement (engaged) position, the two parts 502 clutch the piston rod such that the threads of the two parts engage with the threads of the piston rod 202. As a result, a rotation of the piston rod 202 automatically leads to a translation of this rotational movement to a linear movement of the piston rod 202 in direction 504. Again, the engagement member 400 is fixed with respect to the reservoir part 106, as already mentioned above with respect to FIG. 4.

Besides the possibility that the prestress is the result of an inner prestress of the engagement member 400 that automatically drives the two arms 502 together, it is also possible that, additionally or alternatively, an elastic element 506 is available that connects the two arms with each other and thus urges or biases the two parts 502 towards each other. The elastic element 506 may be for example a spring or a rubber band.

In the example discussed above with respect to FIG. 5, the handle 404 is moved in axial direction of the piston rod 202, i.e. in direction 504. However, as shown in the schematic view of the alternative engagement member of FIG. 6, it is also possible that the two arms 502 of the engagement member 400 have a V-shape as seen in the plane perpendicular to the axis of the piston rod 202. A lateral movement of the mandrel 402 in said plane towards the piston rod 202 thus forces the V-shaped arms to move apart from each other. This again results in a disengagement of the engagement member 400 from the piston rod 202. For example, the movement in direction 604 may be the result of a user-induced push or pull action such that the engagement member can be moved in between the engagement position and the disengagement position at the user's discretion.

Figure 6:
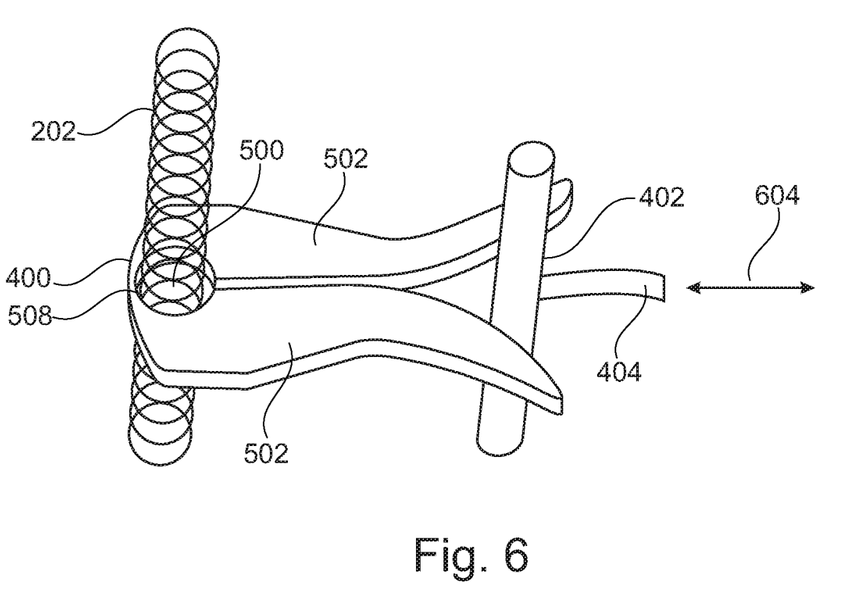
FIG. 6 illustrates a further schematic of an engagement member in the engagement position.

Generally, the two arms 502 are connected with each other via a hinge 508 and the movement in between the engagement position and the disengagement position comprises a rotation of the two arms around said hinge 508.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMERALS

| | |
|---|---|
| 100 | user |
| 102 | portable drug delivery device |
| 104 | driving part |
| 106 | reservoir part |
| 200 | reservoir |
| 202 | piston rod |
| 204 | piston |
| 206 | connecting tube |
| 208 | outlet port |
| 210 | direction |
| 212 | driving mechanism |
| 300 | direction |
| 302 | cannula |
| 304 | septum |
| 306 | skin |
| 308 | base |
| 310 | direction |
| 400 | engagement member |
| 402 | mandrel |
| 404 | handle |
| 406 | axis |
| 408 | counterpart |
| 410 | rotating sleeve |
| 412 | motor |
| 414 | drive screw |
| 416 | direction |
| 500 | threads of the engagement member |
| 502 | arms |
| 504 | direction |
| 506 | elastic element |
| 508 | hinge |
| 604 | direction |

What is claimed is:

1. A portable liquid drug delivery device comprising a reservoir part and a driving part having a drive that produces a torque, the reservoir part comprising:
    a reservoir configured for retaining a liquid drug;
    an outlet port in fluid communication with the reservoir;
    a threaded piston rod with a piston;
    an engagement member having an inner thread configured to engage with the thread of the piston rod in an engaged position and configured to disengage from the thread of the piston rod in a disengaged position, the engagement member being prestressed in the disengaged position to thereby bias the engagement member toward the engaged position, the engagement member further configured to convert the torque of the drive into a linear movement of the piston rod when the engagement member is in the engaged position and wherein the engagement member does not convert the torque of the drive into linear movement of the piston rod when the engagement member is in the disengaged position, wherein the piston is configured, upon the linear movement of the piston rod, to deliver the liquid drug to the outlet port;
    wherein the engagement member is a nut having two parts wherein the two parts of the nut clutch the piston rod in the engaged position and release the piston rod in the disengaged position and wherein each of the two parts of the nut has an arm; and a handle, the handle being moveable from a blocking position between the arms of the nut to prevent movement of the two parts from the disengaged position to the engaged position and a retracted position allowing the two parts to move into the engaged position.

2. The portable drug delivery device of claim 1, wherein the engagement member is configured to automatically move from the disengaged position to the engaged position upon a mechanical coupling of the reservoir part with the driving part.

3. The portable drug delivery device of claim 2, wherein the piston rod is rotatable with respect to the reservoir part and is configured to directly rotatably couple to the drive upon the mechanical coupling of the reservoir part with the driving part, the engagement member being fixed with respect to the reservoir part.

4. The portable drug delivery device of claim 2, wherein the piston rod is non-rotatable with respect to the reservoir part and is configured to indirectly mechanically couple to the drive via the engagement member, wherein the engagement member is configured to directly rotatably couple to the drive upon the mechanical coupling of the reservoir part with the driving part.

5. The portable drug delivery device of claim 1, wherein in the engaged position, the threads of the piston rod fully engage the threads of the engagement member.

6. The portable drug delivery device of claim 1, wherein the prestress of the engagement member is caused by an inner prestress of the engagement member or an elastic element that induces the bias onto the engagement member.

7. The portable drug delivery device of claim 1, wherein the two parts of the nut each have threads that together form the inner thread, wherein the two parts of the nut:
(i) clutch the piston rod in the engaged position such that the threads of the two parts engage with the threads of the piston rod, and
(ii) release the piston rod in the disengaged position such that the threads of the two parts are disengaged from the threads of the piston rod.

8. The drug delivery device of claim 7, wherein the two parts of the nut are joined by a hinge, the engagement member being adapted such that the movement of the engagement member from the disengaged position to the engaged position comprises a swiveling of the two parts towards each other around the hinge.

9. The portable drug delivery device of claim 1, wherein the handle is further configured to automatically move the two parts of the nut apart from each other from the engaged position towards the disengaged position upon a mechanical force acting upon the handle.

10. The portable drug delivery device of claim 1, wherein the handle is pivotably mounted around an axis on the reservoir part, the handle being configured for rotation around the axis between the engaged position and the disengaged position.

11. The portable drug delivery device of claim 1, wherein the handle is mounted on the reservoir part in a laterally movable manner, the lateral movement being a movement in a plane perpendicular to the axis of the piston rod.

12. The portable drug delivery device of claim 1, wherein the driving part is reusable and the reservoir part is disposable.

13. A reservoir part for a portable liquid drug delivery device according to claim 1.

14. A portable liquid drug delivery device comprising a reservoir part and a driving part having a drive that produces a torque, the reservoir part comprising:
a reservoir configured for retaining a liquid drug;
an outlet port in fluid communication with the reservoir;
a threaded piston rod with a piston;
an engagement member having an inner thread configured to engage with the thread of the piston rod in an engaged position and configured to disengage from the thread of the piston rod in a disengaged position, the engagement member being prestressed in the disengaged position to thereby bias the engagement member toward the engaged position, the engagement member further configured to convert the torque of the drive into a linear movement of the piston rod when the engagement member is in the engaged position and wherein the engagement member does not convert the torque of the drive into linear movement of the piston rod when the engagement member is in the disengaged position, wherein the piston is configured, upon the linear movement of the piston rod, to deliver the liquid drug to the outlet port;
wherein the engagement member comprises a nut having two parts each with threads that together form the inner thread, wherein the two parts of the nut:
(i) clutch the piston rod in the engaged position such that the threads of the two parts engage with the threads of the piston rod, and
(ii) release the piston rod in the disengaged position such that the threads of the two parts are disengaged from the threads of the piston rod;
a handle configured in the disengaged position for blocking the movement of the two parts of the nut from the disengaged position to the engaged position; and
wherein each part of the nut has an arm, wherein:
in the disengaged position the handle is located in between the arms and is adapted for blocking the movement of the two parts from the disengaged to the engaged position; and
in the engaged position the handle is retracted from the arms to the extent that the two parts can assume the engaged position.

15. A portable liquid drug delivery device comprising a reservoir part and a driving part having a drive that produces a torque, the reservoir part comprising:
a reservoir configured for retaining a liquid drug;
an outlet port in fluid communication with the reservoir;
a threaded piston rod with a piston;
an engagement member having an inner thread configured to engage with the thread of the piston rod in an engaged position and configured to disengage from the thread of the piston rod in a disengaged position, the engagement member being prestressed in the disengaged position to thereby bias the engagement member toward the engaged position, the engagement member further configured to convert the torque of the drive into a linear movement of the piston rod when the engagement member is in the engaged position and wherein the engagement member does not convert the torque of the drive into linear movement of the piston rod when the engagement member is in the disengaged position, wherein the piston is configured, upon the linear movement of the piston rod, to deliver the liquid drug to the outlet port;
wherein the engagement member comprises a nut having two parts each with threads that together form the inner thread, wherein the two parts of the nut:

(i) clutch the piston rod in the engaged position such that the threads of the two parts engage with the threads of the piston rod, and
(ii) release the piston rod in the disengaged position such that the threads of the two parts are disengaged from the threads of the piston rod; and a handle configured in the disengaged position for blocking the movement of the two parts of the nut from the disengaged position to the engaged position; wherein the handle is further configured to automatically move the two parts of the nut apart from each other from the engaged position towards the disengaged position upon a mechanical force acting upon the handle; and wherein the handle comprises a mandrel configured for being located between the two parts of the nut for blocking the movement of the two parts from the disengaged position to the engaged position, the mandrel and the two parts being shaped such that the mandrel forces the movement of the two parts apart from the engaged position towards the disengaged position upon the mechanical force acting upon the handle.

* * * * *